United States Patent [19]

Shoffner

[11] 4,048,228
[45] Sept. 13, 1977

[54] SUBSTITUTED CYANAMIDIC COMPOUNDS

[75] Inventor: James P. Shoffner, Elk Grove Village, Ill.

[73] Assignee: UOP Inc., Des Plaines, Ill.

[21] Appl. No.: 758,617

[22] Filed: Jan. 12, 1977

Related U.S. Application Data

[63] Continuation-in-part of Ser. No. 611,581, Sept. 8, 1975, abandoned, which is a continuation-in-part of Ser. No. 358,285, May 7, 1973, abandoned.

[51] Int. Cl.$^2$ .......................................... C07C 119/00
[52] U.S. Cl. ................................. 260/566 R; 424/325
[58] Field of Search ................................... 260/566 R

[56] References Cited

U.S. PATENT DOCUMENTS 3,751,412  8/1973  Natsugari et al. ............ 260/566 R X Primary Examiner—Gerald A. Schwartz
Attorney, Agent, or Firm—James R. Hoatson, Jr.; Raymond H. Nelson; William H. Page, II

[57] ABSTRACT

Substituted cyanamidic compounds as exemplified by N-(diphenylmethylidene) cyanamide may be prepared by reacting nitrogen-containing compounds having the formula:

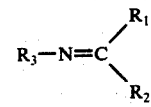

in which $R_1$ and $R_2$ are selected from the group consisting of hydrogen, aryl, alkyl possessing from 1 to about 30 carbon atoms, cycloalkyl possessing from about 5 to about 12 carbon atoms in the ring, alkyl-substituted cycloalkyl, aryl-substituted cycloalkyl, alkaryl and aralkyl radicals and $R_3$ is selected from the group consisting of hydrogen, alkyl possessing from 1 to about 30 carbon atoms, aryl, cycloalkyl possessing from 5 to about 12 carbon atoms in the ring, alkyl-substituted cycloalkyl, aryl-substituted cycloalkyl and bicycloalkyl radicals with cyanamide and a compound selected from the group consisting of an acid-acting compound, an alkyl halide and an alkyl sulfate.

6 Claims, No Drawings

SUBSTITUTED CYANAMIDIC COMPOUNDS

CROSS-REFERENCE TO RELATED APPLICATIONS

This application is a continuation-in-part of copending application Ser. No. 611,581, filed Sept. 8, 1975, now abandoned which is a continuation-in-part of copending application Ser. No. 358,285 filed May 7, 1973 and now abandoned, all teachings of which are incorporated herein by reference thereto.

BACKGROUND OF THE INVENTION

It has been shown in the prior art that various transamination reactions may be effected in the presence of imine compounds. Various compounds which contain a carbon atom doubly bonded to a nitrogen atom may be prepared by reacting a carboxylic acid with a ketimine. For example, U.S. Pat. No. 3,751,412 discloses the reaction of 2-aminophenylbenzyl-idene cyclohexyl imine with aminopropionitrile to produce 2-aminophenyl-benzylideneaminopropionitrile. However, it is to be noted that this reference is limited to the preparation of 2-amino-1,5-benzodiazocine derivatives. The compounds which are set forth in this reference differ from the compounds which are utilized in the present invention due to the presence of methylene groups between two primary functional groups which characterizes the compounds in the instant invention. These compounds cannot be considered mere homologs due to the presence of the methylene groups inasmuch as cyanamide cannot be considered to be a homolog of beta-aminopropionitrile. The differences which exist between the compounds of the present invention and those which are set forth in the aforementioned patent are many and varied in nature. For example, the dissociation constant of the cyanamide which is utilized in the present invention is acidic in nature in contradistinction to the basic dissociation constant which is possessed by the beta-aminopropionitrile.

Another difference which exists between the compounds of the reference and the compounds of the instant invention lies in the resonance capabilities of the compounds. For example, in the case of the aminopropionitrile, the presence of the methylene groups will inhibit the resonance of the compound and disrupt the conjugated system. This disruption of the system will prevent interaction of the functional groups as well as electron delocalization. In contradistinction to this, the compounds of the instant invention will possess the possibility of interaction of the imino and cyano functional groups which should lead to forms such as the following:

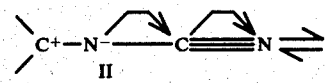

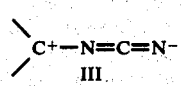

These forms illustrate the novelty and uniqueness which is inherent in the cyanamidic structure of the novel compounds of this invention. For example, the forms as illustrated by Structures II and III are 1,2- and 1,4-dipolar forms respectively and, by nature of their configurations, could be expected to lead to a variety of cycloaddition reactions. The aminopropionitrile could not assume these resonance forms and thus permit a cycloaddition reaction. Another characteristic which Structure III possesses is its ability to take part in the formation of peptides, esters and anhydrides by virtue of its acting as a water acceptor. Aminopropionitrile does not possess this capability.

Likewise, cyanamide may be utilized as a reactant in the preparation of various alkali and alkaline earth metal salts which are stable at standard operating conditions of temperature and pressure while beta-aminopropionitrile cannot be utilized to prepare such salts. It was therefore unexpected that the novel compounds of the present invention which constituted substituted cyanamide compounds could be prepared by reacting cyanamide with the nitrogen-containing compounds hereinafter set forth in greater detail to prepare the desired products.

In addition to the aforementioned differences between cyanamide and the beta-aminopropionitrile which were discussed in the preceding paragraph, it is also noted that the prior art reference is silent as to any transamination between double bonds concerning cyanamide compounds or a preparation of cyanamidic products.

This invention relates to novel substituted cyanamidic compounds. More specifically the invention concerns novel substituted cyanamidic compounds which may be prepared by reacting a nitrogen-containing compound with cyanamide in the presence of an acid-acting compound, an alkyl halide or an alkyl sulfate compound at relatively mild operating conditions of temperature and pressure.

The compounds of the present invention, namely, cyanamidic compounds may be utilized in the chemical industry in many ways. For example, methylidene- or benzylidene-substituted cyanamides may be utilized in the chemical industry as insecticides for the purposes of exterminating ants, flies, rats, mice, moles, or other burrowing insects and rodents; and fumigation of greenhouses, mushroom houses, flower mills, grain and seedmills; for the fumigation of citrus fruit trees to prevent or control insect population thereon; in the leaching of gold and silver ores; etc. It is understood within the scope of this invention that various methylidene-substituted and benzylidene-substituted cyanamides may be used for different purposes. For example the benzylidene cyanamide compounds may be substituted in such a way as to allow the compounds to be utilized as an insect repellant or as a flame retardant composition of matter. Likewise, various methylidene-substituted cyanamides may be utilized for other purposes such as precious metal recovery or in the preparation of various other cyanamides which may be used as catalytic compositions of matter in other various petroleum and hydroformylation reactions.

By utilizing the process herein described, it will be possible to obtain substituted cyanamidic compounds in a more simple process than has hereinbefore been set forth in the prior art. Therefore, the various methylidene- and benzylidene-substituted cyanamides which have been otherwise extremely difficult to obtain may be manufactured in a more economically feasible method as a result of the utilization of smaller quantities of energy output per quantity of dicyanamidic product and the lower capitalization which is necessary to construct a cyanamidic production unit.

It is therefore an object of this invention to obtain a novel substituted cyanamidic compound.

A further object of this invention is to provide a process for the preparation of various substituted cyanamidic compounds by reacting a nitrogen-containing compound with cyanamide in the presence of a third component to obtain the desired product.

In one aspect an embodiment of this invention resides in a substituted cyanamidic compound having the general formula:

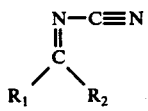

in which $R_1$ and $R_2$ are selected from the group consisting of hydrogen, aryl, alkyl having from 1 to about 30 carbon atoms, cycloalkyl having from about 5 to about 12 carbon atoms in the ring, alkyl-substituted cycloalkyl, aryl-substituted cycloalkyl, aralkyl, and alkaryl radicals.

A specific embodiment of this invention is found in a novel substituted cyanamidic compound such as N-(diphenylmethylidene)cyanamide.

Other objects and embodiments will be found in the following further detailed description of the present invention.

As hereinbefore set forth the present invention is concerned with novel compositions of matter which comprise substituted cyanamidic compounds. These compounds which possess the generic formula:

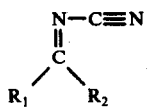

in which $R_1$ and $R_2$ are selected from the group consisting of hydrogen, aryl, alkyl having from 1 to about 30 carbon atoms, cycloalkyl having from about 5 to about 12 carbon atoms in the ring, alkyl-substituted cycloalkyl, aryl-substituted cycloalkyl, aralkyl, and alkaryl radicals are prepared by reacting a nitrogen-containing compound having the formula:

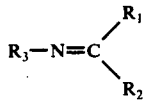

in which $R_1$ and $R_2$ are selected from the group consisting of hydrogen, aryl, alkyl possessing from 1 to about 30 carbon atoms, cycloalkyl possessing from about 5 to about 12 carbon atoms in the ring, alkyl-substituted cycloalkyl, aryl-substituted cycloalkyl, alkaryl and aralkyl radicals and $R_3$ is selected from the group consisting of hydrogen, alkyl possessing from 1 to about 30 carbon atoms, aryl, cycloalkyl possessing from 5 to about 12 carbon atoms in the ring, alkyl-substituted cycloalkyl, aryl-substituted cycloalkyl and bicycloalkyl radicals with cyanamide and a compound selected from the group consisting of an acid-acting compound and an alkyl halide and an alkyl sulfate compound at reaction conditions which comprises a temperature of about 30° to about 70° C. and a pressure of from about 1 atmosphere to about 100 atmospheres. When superatmospheric pressures are employed within the scope of this invention, the superatmospheric pressure may be afforded by the charge or introduction to the reaction zone of a substantially inert gas such as nitrogen, helium, argon, neon, xenon, krypton, or mixtures thereof such as nitrogen-helium, nitrogen-xenon, neon-argon, neon-krypton, helium-neon-krypton, etc.

In a preferred embodiment of the present invention it is disclosed that the reactants comprising the nitrogen-containing compound, cyanamide and a compound selected from the group consisting of an acid-acting catalyst, an alkyl halide and an alkyl sulfate compound must be present in a molar ratio of at least equimolecular proportions. However, the reaction may also be effected utilizing less than equimolecular proportions, the drawback or disadvantage in utilizing such proportions being that it would not be considered to be an economically feasible method for the preparation of the desired compounds. It is also contemplated within the scope of this invention that one or two of any of the reactants may by present in either slight or great excess of the molar proportion of either one or two of the other remaining reactants. This excess molar quantity will not detrimentally effect production of the cyanamidic compound as controlled by the lower molar ratio of one of the three reactants, however, it would be economically unfeasible to conduct the reaction with any excess of one or more of the reactants as a result of the problem of separation of any unconverted reactants from the desired cyanamidic compound.

If so desired, the reaction may be effected in an inert organic reaction medium. Such an inert reaction medium will comprise an alkanol containing from 1 to about 10 carbon atoms such as methanol, ethanol, propanol, butanol, pentanol, hexanol, heptanol, octanol, nonanol, decanol, or branched chained or straight chained liquid alkane compounds such as 2,2,4-trimethylpentane (also known as isooctane), n-hexane, n-heptane, n-nonane, n-octane, n-decane, isohexanes, isoheptanes, isodecanes, isononanes, or other various aromatic inert diluents such as toluene, xylene, pseudocumene, mesitylene, durene, etc.

One reactant which is utilized to prepare the novel compounds of the present invention will comprise a nitrogen-containing compound having the formula:

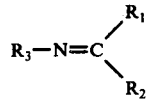

wherein $R_1$ and $R_2$ are selected from the group consisting of a hydrogen, aryl, alkyl possessing from 1 to about 30 carbon atoms, cycloalkyl possessing from about 5 to about 12 carbon atoms, alkyl-substituted cycloalkyl, aryl-substituted cycloalkyl, alkaryl and aralkyl radicals and where $R_3$ is selected from the group consisting of a hydrogen, alkyl possessing from 1 to about 30 carbon atoms, aryl, cycloalkyl possessing from about 5 to about 12 carbon atoms, alkyl-substituted cycloalkyl, aryl-substituted cycloalkyl and bicycloalkyl radicals. Suitable examples of nitrogen-containing compounds may be exemplified by diisopropyl ketone methyl amine (also known as diisopropylmethylidenemethylamine), N-butylpropylmethylideneethylamine (also known as N-ethylpropylbutyl ketimine), N-(di-n-butylmethylidene-phenylamine), N-heptylamylmethylidene-n-butylamine (also known as N-n-butylheptylamyl ketimine), N-methylhexylmethylideneheptylamine (also known as N-heptylmethylhexyl ketimine), N-n-octylideneheptylamine, N-[3-hexylidene]cyclohexylamine (also known as N-cyclohexylethylpropyl ketimine), N-(2-butylidene)octylamine (also known as N-octylmethylethyl ketimine), N-1-butylidenecyclohexylamine, N-(1-pentylpentylidene)-n-propylamine, N-(diphenylmethylidene)cyclohexylamine, N-(dicyclopentylmethylidene)cyclohexylamine, N-(cyclopentylcyclohexylmethylidene)cycloheptylamine, N-(3-decylidene)cyclooctylamine, N-(4-undecylidene)cyclononylamine, N-(4-dodecylidene)cyclodecylamine, N-(5-tridecylidene)cycloundecylamine, N-(2-tetradecylidene)cyclododecylamine, N-(4-pentadecylidene)cyclohexylamine, N-(5-hexadecylidene)-phenylamine, N-(5-heptadecylidene)-2-ethylcyclohexylamine, N-(8-octyldecylidene)-2-tolylamine, N-(6-nonyldecylidene)decylamine, N-(9-eicosylidene) pentadecylamine, N-(8-heneicosylidene)hexadecylamine, N-(10-docosylidene)-o-xylylamine, N-(tricosylidene)eicosylamine, N-(11-tetracosylidene)cyclopentylamine, N-(10-pentacosylidene)cyclohexylamine, N-(hexacosylidene)pentacosylamine, N-(heptacosylidene)hexacosylideneamine, N-(octacosylidene)-phenylamine, N-(2-ethylpentyl)cyclohexylmethylidenecyclohexylamine, N-(m-xylyl-o-tolylmethylidene)-p-xylylamine, N-(dicyclopentylmethylidene)-n-pentylamine, N-(dicyclohexylmethylidene)cyclohexylamine, N-(dicycloheptylmethylidene)phenylamine, N-(dicyclooctylmethylidene)ethylamine, N-(dicyclopentylmethylidene)-2-ethylcyclohexylamine, N-(2-butylidene)-m-tolylamine, N-(di-n-amylmethylidene)cyclohexylamine, N-(2-butylidene)-alpha-bicyclopentylamine, N-(diphenylmethylidene)-alpha-naphthylamine, N-butylidene-beta-naphthylamine, etc.

The nitrogen-containing compound of the type hereinbefore set forth in greater detail is reacted with cyanamide with possesses the following formula: $H_2=N-C\equiv N$ and a compound selected from the group consisting of an acid-acting compound, an alkyl halide and an alkyl sulfate compound. The acid-acting compound may be defined as either a Bronsted acid (proton donor) or a Lewis acid (electron acceptor). Specific examples of Bronsted acids would include both inorganic and organic acids; the inorganic acids may be exemplified by hydrogen chloride, sulfuric acid, nitric acid, selenium acid, phosphoric acid, arsenic acid, antimony acid, while the organic acids may be exemplified by formic acid, acetic acid, propionic acid, n-butyric acid, isobutyric acid, n-valeric acid, trimethylacetic acid, caproic acid, n-heptylic acid, caprylic acid, fluoroacetic acid, trifluoroacetic acid, chloroacetic acid, trichloroacetic acid, bromoacetic acid, tribromoacetic acid, iodoacetic acid, triiodoacetic acid, dichloroacetic acid, dibromoacetic acid, difluoroacetic acid, diiodoacetic acid, alpha-chloropropionic acid, beta-chloropropionic acid, glycolic acid, lactic acid, methoxyacetic acid, thioglycolic acid, cyanoacetic acid, glyoxylic acid, malonic acid, acrylic acid, vinylacetic acid, phenylacetic acid, etc. Specific examples of Lewis acids will include metal halides such as tin chloride, tin bromide, tin iodide, aluminum chloride, aluminum bromide, aluminum iodide, germanium chloride, germanium bromide, germanium iodide, antimony chloride, antimony bromide, antimony iodide, zinc chloride, zinc bromide, zinc iodide, etc. Suitable examples of alkyl halides will include methyl chloride, ethyl chloride, propyl chloride, butyl chloride, pentyl chloride, hexyl chloride, heptyl chloride, octyl chloride, nonyl chloride, decyl chloride, methyl bromide, ethyl bromide, propyl bromide, butyl bromide, pentyl bromide, hexyl bromide, heptyl bromide, octyl bromide, nonyl bromide, decyl bromide, methyl iodide, ethyl iodide, propyl iodide, butyl iodide, pentyl iodide, hexyl iodide, heptyl iodide, octyl iodide, nonyl iodide, decyl iodide, etc., or such alkyl sulfate compounds as methyl sulfate, ethyl sulfate, propyl sulfate, butyl sulfate, pentyl sulfate, hexyl sulfate, heptyl sulfate, octyl sulfate, nonyl sulfate, decyl sulfate, etc.

It is understood that the aforementioned inert organic reaction mediums, Bronsted acids, Lewis acids, alkyl halides, sulfate halides and nitrogen-containing compounds are only representative of the class of compounds which may be employed and that the present invention is not necessarily limited thereto.

The novel compounds of the present invention may be prepared utilizing a process which may comprise either a batch or continuous type operation. For example, when a batch type operation is employed, the reactants comprising the nitrogen-containing compound, cyanamide and the compound selected from the group consisting of an acid-acting compound, an alkyl halide and an alkyl sulfate compound are placed in an appropriate apparatus containing an organic inert reaction medium, if one is so desired. If atmospheric pressure is to be employed, the reaction vessel is then heated to a predetermined operating temperature. After maintaining the reactants in the reaction vessel at this temperature for a reaction time which may range from 0.5 up to 20 hours or more in duration, the heating is discontinued and the vessel is allowed to return to room temperature. The resultant cyanamidic product is then separated from the reaction medium and the resultant monosubstituted amine salt formed in the reaction and the cyanamidic product are subjected to conventional means of purification and separation, said means including washing, drying, extraction, evaporation, fractional distillation, etc., whereby the desired substituted cyanamidic compound is recovered. The process of the present invention is contemplated to be effected at room temperature and pressure in which case the reactants are allowed to mix at room temperature and pressure in an inert organic reaction medium for a period of time of from about 0.5 to about 20 hours or more and recovered as hereinbefore outlined. If superatmospheric pressures are to be employed in the reaction, the reactants are charged to a pressure vessel such as a rotating autoclave which contains an inert organic medium such as a benzene-methanol mixture. The autoclave is sealed and a substantially inert gas such as nitrogen or helium is pressed until the desired operating pressure is reached. The autoclave is then heated to the desired operating temperature or, if no elevated temperature is desired, the vessel may be maintained at room temperature and held thereat for a predetermined residence time. At the end of this time, heating is terminated if it was so desired, the autoclave is allowed to return to room temperature and the excess pressure is discharged allowing the autoclave to return to ambient pressure. The autoclave is opened and the reaction mixture is treated as hereinbefore set forth whereby the desired products, namely, the substituted cyanamidic compounds are separated and recovered from the autoclave.

It is also contemplated within the scope of this invention that the process for obtaining the substituted cyanamidic compound may be effected in a continuous manner of operation. When such a type of operation is employed, the reactants, the nitrogen-containing compound, cyanamide and the compound selected from the group consisting of an acid-acting compound, an alkyl halide and an alkyl sulfate compound are continuously charged to the reaction vessel containing an inert organic reaction medium, said vessel being maintained at proper operating conditions of temperature and pressure. After completion of the desired residence time, the reactor effluent is continuously withdrawn and subjected to conventional means of separation whereby the desired substituted cyanamidic compound is recovered, while any unreacted starting materials are recycled to the reaction zone to form a portion of the feedstock. It should be noted that a secondary product formed from the reaction of the cyanamide, nitrogen-containing compound and the compound selected from the group consisting of an acid-acting compound, an alkyl halide and an alkyl sulfate compound is an amine salt which can be separated from the substituted cyanamidic compound by distillation, drying, washing, or filtration and utilized either in a different charge stock to prepare other aminated compounds or sold as a secondary product, thereby mitigating the cost of production.

Examples of substituted cyanamidic compounds which are prepared by the process of this invention will comprise any compounds in accordance with the following formula:

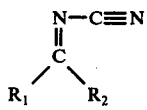

wherein $R_1$ and $R_2$ are selected from the group consisting of hydrogen, aryl, alkyl possessing from 1 to about 30 carbon atoms, cycloalkyl possessing from about 5 to about 12 carbon atoms, alkyl-substituted cycloalkyl, aryl-substituted cycloalkyl, alkaryl and aralkyl radicals. Suitable examples of substituted cyanamidic compounds may be exemplified by butylidene cyanamide, methylidene cyanamide, ethylidene cyanamide, propylidene cyanamide, pentylidene cyanamide, hexylidene cyanamide, heptylidene cyanamide, octylidene cyanamide, nonylidene cyanamide, decylidene cyanamide, undecylidene cyanamide, dodecylidene cyanamide, tridecylidene cyanamide, tetradecylidene cyanamide, pentadecylidene cyanamide, hexadecylidene cyanamide, heptadecylidene cyanamide, octadecylidene cyanamide, nonadecylidene cyanamide, eicosylidene cyanamide, heneicosylidene cyanamide, docosylidene cyanamide, tricosylidene cyanamide, tetracosylidene cyanamide, pentacosylidene cyanamide, hexacosylidene cyanamide, heptacosylidene cyanamide, octacosylidene cyanamide, nonacosylidene cyanamide, tricontylidene cyanamide, benzylidene cyanamide, 2-toluidine cyanamide, 4-tolylidene cyanamide, 2,3-xylidene cyanamide, dicyclopentylmethylidene cyanamide, cyclopentylcyclohexylmethylidene cyanamide, 2-methylpentyl-3-ethylcyclohexylmethylidene cyanamide, 2-phenylcyclopentyl-2-methylcyclohexylmethylidene cyanamide, N-(diphenylmethylidene) cyanamide, N-(di-n-butylmethylidene)cyanamide, N-(dicyclopentylmethylidene)cyanamide, etc.

It is to be understood that the foregoing examples of substituted cyanamidic compounds which are prepared by the process of this invention are only representative of those compounds which may be prepared and that the hereinbefore set forth list is not intended to be limited within the scope of the general generic disclosure.

The following examples are given to illustrate types of novel substituted cyanamidic compounds and to a process for the preparation thereof. However, these examples are given merely for purposes of illustration and are not intended to limit the generally broad scope of the present invention in strict accordance therewith.

EXAMPLE I

To illustrate the preparation of a novel substituted cyanamidic compound, 2.1 grams (0.05 mole) of cyanamide, 5.7 grams (0.05 mole) of trifluoroacetic acid and 13.15 grams (0.05 mole) of N-(diphenylmethylidene)cyclohexylamine were added to a round bottomed flask containing 50 ml of methanol. The flask was maintained at ambient temperature and pressure for a period of time comprising 6 hours, during which the contents of the flask were allowed to remain stagnant. The reaction mixture was concentrated and treated with a mixture of hexane-benzene in a 1:1 volume proportion. The solid precipitate was recovered, analyzed and found to be cyclohexylamine trifluoroacetate. The filtrate was concentrated to a heavy syrup whereupon it crystallized and was analyzed by means of nuclear magnetic resonance spectroscopy which showed a heavy aryl absorption from 6.90 δ to 7.90 δ and by infrared spectroscopy instrumentation which showed bands for carbon to nitrogen doubly-bonded at 1555 cm$^{-1}$ and a carbon to nitrogen triple bond at 2200 cm$^{-1}$. The above set forth analyses indicate the structure to be N-(diphenylmethylidene)cyanamide, the total reaction being set forth as:

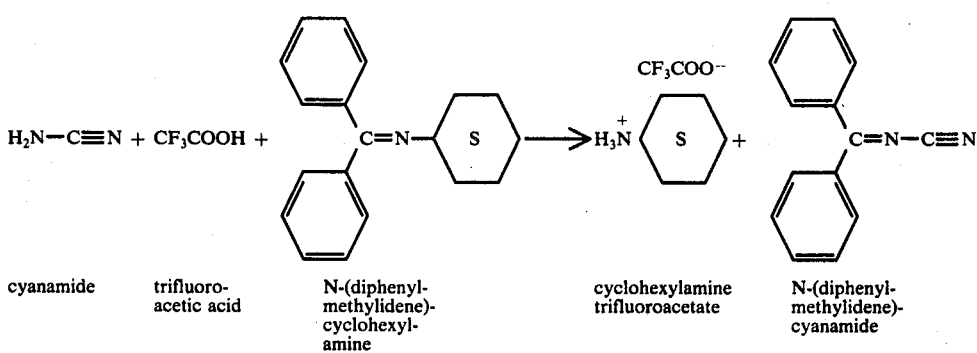

EXAMPLE II

To illustrate the preparation of a different novel substituted cyanamidic compound 0.84 grams (0.02 mole) of cyanamide, 2.28 grams (0.02 mole) of trifluoroacetic acid and 3.22 grams (0.02 mole) of N-(benzylidene)-t-butylamine were added to a round bottomed flask containing 50 milliliters of benzene. The flask was maintained at ambient temperature and pressure for a period of time comprising 8 hours, during which time the contents of the flask were left stagnant. The reaction mixture was concentrated and treated with a mixture of hexane-benzene in a 1:1 volume proportion. The solid precipitate was recovered and identified as the t-butylamine salt of trifluoroacetic acid. The filtrate was concentrated to a heavy syrup whereupon it crystallized and was analyzed by means of nuclear magnetic resonance spectroscopy instrumentation which showed resonance from 7.33 $\delta$ to 8.03 $\delta$ (5 protons) and a singlet at 8.93 $\delta$ (1 proton). The filtrate was further analyzed by means of infrared spectroscopy instrumentation, said analysis showed a spectrum with an absorbence at 1570 cm$^{-1}$ and 1595 cm$^{-1}$ indicating a carbon to nitrogen double bond and at 2195 cm$^{-1}$ indicating a carbon to nitrogen triple bond. The analyses indicated that the reaction product is N-(benzylidene)cyanamide formed in accordance with the following reaction:

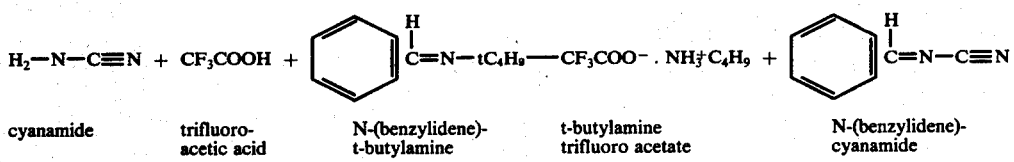

| cyanamide | trifluoro-acetic acid | N-(benzylidene)-t-butylamine | t-butylamine trifluoro acetate | N-(benzylidene)-cyanamide |

EXAMPLE III

In like manner equimolecular proportions of methyl iodide cyanamide and N-(dicyclopentylmethylidene)-n-pentylamine may be mixed in an 850 ml rotating autoclave in the absence of any inert organic reaction medium. The reactants may be allowed to mix for approximately 5 hours at a temperature of 60° C. and an initial pressure of 5 atmospheres of nitrogen. At the end of the 5-hour period of time, the autoclave may be allowed to return to room temperature and the excess pressure may be discharged. The autoclave may then be opened and the reaction product removed therefrom. The product may then be analyzed by means of gas-liquid chromatography to determine the presence of the desired product, namely, N-(dicyclopentylmethylidene)cyanamide.

EXAMPLE IV

In this example equimolecular proportions of anhydrous hydrochloric acid and N-(di-n-butylmethylidene)phenylamine may be mixed in an inert organic medium comprising ethanol, the resulting mixture being contained in a 250 ml flask. Following this, an initial molecular proportion of cyanamide may be added to the mixture and the reactants may be thoroughly admixed for a period of 5 hours. At the end of the 5-hour period, the reaction product may be recovered and analyzed by means of gas-liquid chromatography to determine the presence of the desired product comprising N-(di-n-butylmethylidene)cyanamide.

EXAMPLE V

In a manner similar to that set forth in the above examples, equimolecular proportions of cyanamide, trifluoroacetic acid and N-butylmethylidenecyclohexylamine may be added to a 250 ml flask containing methanol. The reactants may be thoroughly admixed while maintaining the flask at ambient temperatures and pressures for a period of 6 hours. At the end of the 6-hour period, mixing may be discontinued and the reaction mixture recovered. The reaction product may then be subjected to gas-liquid chromatography to determine the presence of the desired product comprising N-(butylidene)cyanamide.

I claim as my invention:

1. A substituted cyanamidic compound having the general formula:

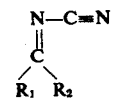

in which $R_1$ and $R_2$ are selected from the group consisting of hydrogen, aryl, alkyl having from 1 to about 30 carbon atoms, cycloalkyl having from 5 to 12 carbon atoms in the ring, alkyl-substituted cycloalkyl, aryl-substituted cycloalkyl, aralkyl, and alkaryl radicals.

2. The cyanamidic compound of claim 1 being N-(diphenylmethylidene)cyanamide.

3. The cyanamidic compound of claim 1 being N-(di-n-butylmethylidene)cyanamide.

4. The cyanamidic compound of claim 1 being N-(dicyclopentylmethylidene)cyanamide.

5. The cyanamidic compound of claim 1 being N-(benzylidene)cyanamide.

6. The cyanamidic compound of claim 1 being N-(butylidene)cyanamide.

* * * * *